United States Patent [19]

Barrows et al.

[11] Patent Number: 5,372,802
[45] Date of Patent: Dec. 13, 1994

[54] STABILIZED PEROXIDE GELS CONTAINING FLUORIDE

[75] Inventors: Stephen R. Barrows, Trumbull; Christine W. Ryles, Milford; David R. Williams, Monroe, all of Conn.

[73] Assignee: Chesebrough-Pond's USA Co., Division of Conopco, Inc., Greenwich, Conn.

[21] Appl. No.: 116,092

[22] Filed: Sep. 2, 1993

[51] Int. Cl.$^5$ .................. A61K 7/16; A61K 7/18; A61K 7/20; A61K 33/40
[52] U.S. Cl. ..................... 424/52; 424/49; 424/53; 424/613; 424/616
[58] Field of Search ................... 424/49-88, 424/52, 53

[56] References Cited

U.S. PATENT DOCUMENTS

| | | |
|---|---|---|
| 2,680,674 | 6/1954 | Cooper et al. ............. 23/207.5 |
| 3,577,521 | 5/1971 | Scheller et al. . |
| 4,100,269 | 7/1978 | Pader . |
| 4,130,501 | 12/1978 | Lutz et al. . |
| 4,343,785 | 8/1982 | Schmolka . |
| 4,477,438 | 10/1984 | Willcockson ............. 424/130 |
| 4,487,757 | 12/1984 | Kiozpeoplou . |
| 4,528,180 | 7/1985 | Schaeffer . |
| 4,537,765 | 8/1985 | Gaffar et al. ............. 424/53 |
| 4,557,935 | 12/1985 | af Ekenstam ............. 424/130 |
| 4,687,663 | 8/1987 | Schaeffer . |
| 4,788,052 | 11/1988 | Ng et al. . |
| 4,837,008 | 6/1989 | Rudy et al. . |
| 4,839,156 | 6/1989 | Ng et al. . |
| 4,839,157 | 6/1989 | Ng et al. . |
| 4,849,213 | 7/1989 | Schaeffer . |
| 4,895,721 | 1/1990 | Drucker . |
| 4,937,066 | 6/1990 | Vlock ..................... 424/52 |
| 4,980,152 | 12/1990 | Frazier et al. ............. 424/52 |
| 5,015,466 | 5/1991 | Parran et al. ............. 424/52 |
| 5,015,467 | 5/1991 | Smitherman ............. 424/52 |
| 5,037,633 | 8/1991 | Ziemkiewicz et al. . |
| 5,037,634 | 8/1991 | Williams et al. . |
| 5,059,417 | 10/1991 | Williams et al. . |
| 5,085,853 | 2/1992 | Williams et al. . |
| 5,094,845 | 3/1992 | Vlock ..................... 424/52 |
| 5,104,644 | 4/1992 | Douglas . |
| 5,165,914 | 11/1992 | Vlock ..................... 424/52 |
| 5,217,710 | 6/1993 | Williams et al. . |
| 5,256,402 | 10/1993 | Prencipe et al. ............. 424/53 |

*Primary Examiner*—Shep K. Rose
*Attorney, Agent, or Firm*—Milton L. Honig

[57] ABSTRACT

An oral composition and method is provided that includes a peroxygen compound such as hydrogen peroxide, a fluoride-containing anticaries agent and a zinc compound such as zinc citrate. The presence of the zinc compound inhibits decomposition that ordinarily would be induced by the presence of fluoride.

17 Claims, No Drawings

STABILIZED PEROXIDE GELS CONTAINING FLUORIDE

BACKGROUND OF THE INVENTION

1. Field of the Invention

The invention relates to dental products for promoting health in the oral cavity.

2. The Related Art

Oral compositions containing both a peroxide and sodium bicarbonate have been acclaimed by the dental profession, especially through the work of Keyes. See Keyes et al. "Periodontics and Oral Hygiene", January 1978, pages 51–56. Formulations based on the Keyes technology, especially the peroxide component, are particularly prone to decomposition. The literature has reported considerable research directed at the stability problem. For instance, see U.S. Pat. Nos. 3,577,521 (Scheller), 4,837,008 (Rudy et al), 4,130,501 (Lutz), 4,895,721 (Drucker) and 4,343,785 (Schmolka). A quite successful approach to the problem has involved physical segregation of the peroxide into a compartment separate from co-reactive ingredients. U.S. Pat. Nos. 4,849,213, 4,687,663 and 4,528,180, all to Schaeffer, disclose a package with a dual-compartment respectively storing a peroxide gel and a bicarbonate paste.

Related technology is described in U.S. Pat. No. 4,487,757 (Kiozpeoplou) which describes a toothpaste in a dispenser that physically separates sodium bicarbonate from acidic ingredients, e.g. citric or ascorbic acids, to prevent contact therebetween prior to usage.

In U.S. Pat. Nos. 4,788,052, 4,839,156 and 4,839,157 (all to Ng et al) are described aqueous hydrogen peroxide gel dentifrices that can be stabilized by use of a combination of hydrophillic and hydrophobic fumed silica. Aqueous mouthrinses have been described in U.S. Pat. No. 5,104,644 (Douglas) that contain hydrogen peroxide. Also present at relatively low concentrations are such additives as zinc chloride, surfactant, sodium citrate and citric acid. It should be noted that neither the Ng et al nor Douglas patents include fluoride anions within the suggested compositions.

From the aforementioned art, it becomes apparent that hydrogen peroxide compositions should be formulated as simply as possible to minimize potential interactions between the peroxide and the remaining ingredients.

Fluoride anion is known by those skilled in the art as a destabilizing factor in peroxide gels. The desirability of achieving anticaries protection for oral products has prompted formulators to seek a satisfactory means to allow fluoride incorporation. In U.S. Pat. Nos. 5,037,633 and 5,037,634 to Williams et al. and Ziemkiewicz et al., respectively, the problem was solved by incorporating sodium fluoride into a bicarbonate paste intended to be co-extruded with a peroxide gel, each from a separate compartment of a dual-compartment container. See also U.S. Pat. No. 5,059,417 (Williams et al.) detailing the peroxide technology.

While relegating fluoride to the bicarbonate component may solve the anticaries problem, there still remains the problem of dispensing a constant volume of both peroxide gel and bicarbonate paste; accurate dosage of fluoride based on total dentifrice volume is thereby ensured. Only with a special, costly pump is such precise delivery achievable.

Consequently, a system has been sought which permits both the bicarbonate and the peroxide components to each incorporate an identical fluoride anticaries agent thereby eliminating need for a costly pump.

Beyond stabilization, any new anticaries system must have consumer satisfactory taste and have no disruptive influence upon rheology, product color or other physical parameters.

Recently it has been reported in U.S. Pat. No. 5,217,710 (Williams et al) that tin compounds, especially stannous ion, may stabilize hydrogen peroxide in the presence of a fluoride compound. Unfortunately, there are two problems with this technology. The first is that stannous ions impart an unsatisfactory metallic taste to the otherwise fine organoleptic properties of the dental compositions. Secondly, the tin compounds have caused severe corrosive pitting of stainless steel reactors in which the dental products were manufactured.

Accordingly, it is an object of the present invention to provide a peroxide-containing composition capable of use with a bicarbonate composition wherein both compositions contain a fluoride anticaries agent and there is no adverse effect upon product stability.

A further object of the present invention is to provide a peroxide composition and a bicarbonate composition held in separate compartments of a dual-compartment delivery system wherein each of the compositions contains an identical fluoride anticaries agent.

A still further object of the present invention is to provide a peroxide composition that incorporates a fluoride anticaries agent such that the composition has consumer-acceptable taste and maintains color, e.g. blue.

A still further object of the present invention is to provide a peroxide gel composition including a fluoride anticaries agent and a stabilizing system that inhibits peroxide decomposition while still maintaining a clear gel.

A still further object of the present invention is to provide a peroxide composition that incorporates a fluoride anticaries agent and a stabilizing system that has no adverse corrosive effect upon stainless steel manufacturing vessels.

Another object of the present invention is to provide a method for inhibiting caries and also promoting gum health through application of a peroxide and a bicarbonate composition, each containing a fluoride compound and each delivered simultaneously from separate compartments of a dual-compartment dispenser.

These and other objects of the present invention will become more readily apparent upon consideration of the more detailed description and Examples which follow.

SUMMARY OF THE INVENTION

An oral composition is provided comprising:
(i) from about 0.1 to about 10% by weight of a peroxygen compound;
(ii) a physiologically-acceptable fluoride-containing compound present in an effective amount to inhibit formation of caries on teeth; and
(iii) a zinc compound present in an effective amount to stabilize the peroxygen compound against decomposition by the fluoride-containing compound.

A method is also provided for stabilizing peroxygen compounds against decomposition, the method including applying to the teeth a composition comprising:
(i) from about 0.1 to about 10% by weight of a peroxygen compound;

(ii) a physiologically-acceptable fluoride-containing compound present in an effective amount to inhibit formation of caries on teeth; and
(iii) a zinc compound present in an effective amount to stabilize the peroxygen compound against decomposition by the fluoride-containing compound.

DETAILED DESCRIPTION

Now it has been discovered that zinc compounds have the unexpected ability to stabilize hydrogen peroxide in the presence of a fluoride compound such as sodium fluoride.

Thus, as a first essential component there is required a compound, especially a salt, delivering zinc ions. By the term "zinc ion" is meant that the zinc-atom portion of a molecule of the zinc compound in the solid or undissociated state, is capable of being dissociated into simple or complex zinc ions, especially when dispersed in an aqueous medium. Examples of the compounds that may be employed are zinc salts of the following inorganic ions: borate, bromide, carbonate, hexafluorosilicate, pyrophosphate, silicate, sulphate and titanate. Organic anions are those having from 2 to 22 carbon atoms with a charged group selected from carboxylate, sulphonate, sulphate and phosphate. Specific examples include, but are not limited to, acetate, benzoate, citrate, glycinate, lactate, phenolsulphonate, salicylate, tartrate, acetylacetonate, maleate, succinate, ascorbate, and gluconate. Most preferred is zinc citrate.

The zinc salts will generally be present in the dental compositions of the invention in an amount from about 0.01 to about 10%, preferably between about 0.1 and 5%, optimally between about 0.2 and 1% by weight. When it is desired to have a clear (at least translucent) gel, the level of zinc salt should range from about 0.1 to 0.5%.

Another important component of the oral composition is that of a fluoride anticaries compound. Illustrative of fluoride compounds are sodium fluoride, potassium fluoride, calcium fluoride, magnesium fluoride, stannous fluoride, stannous monofluorophosphate, sodium monofluorophosphate and copper fluoride. These sources should release anywhere from about 25 to 3500 ppm of fluoride ion. The anticaries agent will be present in an amount from about 0.01 to about 5%, preferably from about 0.1 to about 2.5%, optimally between about 0.2 and about 1.5% by weight of the peroxide composition.

A variety of peroxygen compounds may be employed including urea peroxide, calcium peroxide, hydrogen peroxide and the salts of perborate, persilicate, perphosphate and percarbonate. The most suitable for this invention is hydrogen peroxide. The amount of the peroxygen compound may range from about 0.1 to about 10% by weight. In terms of active weight hydrogen peroxide, the amount will range from about 0.5 to about 5%, preferably from about 0.8 to about 4%, optimally between about 1 and 3% by weight.

Oral compositions of the present invention may be in the form of either a toothpaste, a gel, a tablet, a powder or a mouthwash.

Water may be present in the compositions in amounts ranging from about 20 to about 95% by weight. When the peroxide composition is a gel, the amount of water may range from about 30 to about 55%, optimally between about 35 and 45% by weight.

Structurants are necessary where the peroxide composition is in the form of a gel. Most suitable as the structurant are the polyoxyethylene-polyoxypropylene copolymers where the hydrophobic portion, represented by $(C_3H_6O)$, has a molecular weight ranging from about 2,750 to 4,000 and the hydrophilic portion, represented by $(C_2H_4O)$, constitutes about 70 to 80% of the weight of the copolymer. Commercially the copolymers are available from the BASF Corporation under the trademark, Pluronic ® F88, F99, F108 and F127. Most preferred is Pluronic ® F127 (hereinafter referred to by its CTFA name, Poloxamer ® 407) which has a molecular weight ranging from about 10,000 to 15,000, and containing about 70% of the hydrophilic polyoxyethylene moiety. Amounts of the copolymer can range anywhere from 18 to 25% by weight, preferably between 19 and 24%. Poloxamers are particularly suitable for this invention because of their wide pH tolerance, good compatibility with hydrogen peroxide and unique gel properties.

Glycerol is another preferred ingredient of the peroxide composition when in gel or rinse form. Amounts of glycerol may range from about 5 to about 50%, preferably from about 5 to 20% by weight for the rinse and from about 35 to 45% by weight for the gel.

Adjunct minor ingredients may also be present in the compositions of this invention. Included may be small amounts of colorant, flavor and antioxidant.

Oral compositions of the present invention may include, besides a peroxide composition, an additional separate bicarbonate-containing composition, each held within a separate container available for simultaneous delivery in substantially equal volumes for use in the mouth.

The bicarbonate composition will also contain a fluoride anticaries compound selected from the same fluoride compounds in essentially identical amounts to those described hereinabove with respect to the peroxide composition. Especially preferred is sodium fluoride. Bicarbonate salts will be present in alkalimetal form, examples of which are sodium and potassium. Typically, the concentration of bicarbonate salt will range from about 0.5 to about 80%, preferably from about 5 to about 50%, optimally between about 8 and about 20% by weight of the total combined dental product. The pH of the bicarbonate composition may range from about 7.0 to about 9.5, most preferably about 8.0 to 9.0. When the bicarbonate composition is in toothpaste or gel form, there will typically be included a natural or synthetic thickening agent in an amount from about 0.1 to 10%, preferably about 0.5 to 5% by weight. Thickeners may include hydroxypropyl methyl cellulose, hydroxyethyl cellulose, sodium carboxymethyl cellulose, xanthan gum, tragacanth gum, karaya gum, arabic gum, Irish moss, starch, alginates and carrageenans.

Surfactants are normally also included in the bicarbonate compositions. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to about 5% by weight.

When in the form of a toothpaste or gel, the bicarbonate compositions will normally include an abrasive in addition to the bicarbonate. Abrasives may be selected from water-insoluble alkali or alkaline earth metal salts of metaphosphate (IMP), calcium carbonate, aluminate and silicate. Especially preferred are silica, dicalcium phosphate and calcium carbonate. Amounts of the abrasive will range from about 5 to about 80% by weight.

Tartar control agents may be incorporated into compositions of this invention. Especially effective will be agents containing phosphorous. Inorganic phosphorous tartar control agents may include sodium tripolyphosphate or any of the water-soluble pyrophosphates such as disodium pyrophosphate, dipotassium pyrophosphate and mixtures of these with tetrapotassium pyrophosphates or tetrasodium pyrophosphates. Organic phosphorous compounds that may serve as tartar control agents include polyphosphonates such as disodium ethane-1-hydroxy-1,1-diphosphonate (EHDP), methanediphosphonic acid, and 2-phosphonobutane-1,2,4-tricarboxylic acid.

Flavors are usually present in both the peroxide and, when suitable, bicarbonate compositions. These flavors may be based on oils of spearmint and peppermint. Examples of other flavoring materials include menthol, clove, wintergreen, eucalyptus and aniseed. Flavors may range in concentration from about 0.1 to about 5% by weight of the total composition.

Sweetening agents such as saccharin, sodium cyclamate, aspartame, sucrose and the like may be included at levels from about 0.1 to about 5% by weight of the total composition.

Other additives may also be incorporated into the oral compositions including preservatives, silicones, other synthetic or natural polymers such as Gantrez S-97 ®, and antigingivitis actives.

The following examples will more fully illustrate the embodiments of this invention. All parts, percentages and proportions referred to herein and in the appended claims are by weight of the total composition unless otherwise stated.

EXAMPLE 1

Typical of the present invention is a peroxide gel composition whose formulation is detailed under Table I. The formulation of Table I may be utilized in combination with a bicarbonate composition detailed under Table II, each of the compositions being held in a separate compartment of a dual-compartment dispenser.

TABLE I

| Peroxide Gel Component | |
| --- | --- |
| Ingredient | Wt. % |
| Pluronic F127 | 20.000 |
| Glycerin | 40.000 |
| Hydrogen Peroxide (35% food grade) | 4.285 |
| Citric Acid | 0.600 |
| Sodium Fluoride | 0.240 |
| Zinc Citrate | 0.200 |
| FD&C Blue 1 | 0.005 |
| Phosphoric Acid (85% w/w) | 0.150 |
| Deionized water | Balance |

TABLE II

| Bicarbonate Paste Component | |
| --- | --- |
| Ingredient | Wt. % |
| Polyol II (sorbitol and other sugars) | 48.710 |
| Syloid 63XX (abrasive silica) | 15.000 |
| Sodium Bicarbonate | 10.000 |
| PEG 32 (polyethylene glycol) | 5.000 |
| Sylox 15x (thickening silica) | 4.600 |
| Sodium Lauryl Sulfate | 2.980 |
| SD Alcohol 38B | 2.850 |
| Cellulose Gum | 0.800 |
| Menthol | 0.500 |
| Sodium Saccharin | 0.500 |
| Sodium Fluoride | 0.240 |
| Titanium Dioxide | 0.300 |

TABLE II-continued

| Bicarbonate Paste Component | |
| --- | --- |
| Ingredient | Wt. % |
| Deionized water | Balance |

EXAMPLE 2

A series of stability experiments were conducted to evaluate the effect of zinc citrate on stabilizing a peroxide gel when fluoride ions are present in the composition.

The test employed was the Peroxide Stability/Stress Test (PSST). Samples were exposed to accelerated aging at a temperature of 95° C. over a 6-hour period. These aging conditions were found to have good correlation with 3-month storage stability testing at 105° F. Peroxide content of the gel was assayed by oxidizing potassium iodide to iodine and titrating with sodium thiosulphate on an auto-titrator fitted with a redox electrode.

TABLE III

| PSST Results | | | |
| --- | --- | --- | --- |
| | Initial % $H_2O_2$ | After 6 Hours at 95° C. | % Recovery |
| No Fluoride | | | |
| 1 Month at RT | 1.48 | 1.36 | 91.89 |
| 1 Month at 105° F. | 1.47 | 1.34 | 91.16 |
| Fluoride (0.24% NaF) with Zinc | | | |
| 1 Month at RT | 1.46 | 1.46 | 100.00 |
| 1 Month at 105° F. | 1.47 | 1.43 | 95.97 |
| Fluoride (0.24% NaF) Without Zinc | | | |
| 1 day at RT | 1.58 | 1.04 | 65.82 |
| 3 days at RT | 1.52 | 0.63 | 41.45 |

Table III provides stability results on the composition outlined in Table I of Example 1 (with and without fluoride). From the results it can be seen that zinc citrate has a stablizing effect upon the gel composition in the presence of fluoride ion. Excellent % recovery of hydrogen peroxide is achieved despite storage of the formula (Table I) at 105° F. for extended periods of time.

The foregoing description and Examples illustrate selected embodiments of the present invention. In light thereof, various modifications will be suggested to one skilled in the art, all of which are within the spirit and purview of this invention.

What is claimed is:
1. An oral composition comprising:
   (i) from about 0.1 to about 10% by weight of a peroxygen compound selected from the group consisting of urea peroxide, calcium peroxide, hydrogen peroxide, salts of perborate, salts of persilicate, salts of perphosphate and salts of percarbonate;
   (ii) from about 0.01 to about 5% by weight of a physiologically-acceptable fluoride-containing compound to inhibit formation of caries on teeth selected from the group consisting of sodium fluoride, potassium fluoride, calcium fluoride, magnesium fluoride, stannous fluoride, stannous monofluorophosphate, sodium monofluorophosphate and copper fluoride; and
   (iii) from about 0.01 to about 10% by weight of a zinc compound to stabilize the peroxygen compound against decomposition by the fluoride-containing compound, the zinc compound being selected from the group consisting of zinc borate, zinc bromide, zinc carbonate, zinc hexafluorosilicate, zinc pyrophosphate, zinc silicate, zinc sulphate, zinc titanate, zinc acetate, zinc benzoate, zinc citrate, zinc glycinate, zinc lactate, zinc phenolsulphonate, zinc salicylate, zinc tartrate, zinc acetylacetonate, zinc maleate, zinc succinate, zinc ascorbate, and zinc gluconate.

2. A composition according to claim 1 wherein the fluoride anticaries agent is sodium fluoride.

3. A composition according to claim 1 wherein the zinc compound is zinc citrate.

4. A composition according to claim 1 wherein the zinc compound is present in an amount from about 0.01 to 0.5% by weight.

5. A composition according to claim 4 wherein the oral composition is a clear gel.

6. A method for stabilizing peroxygen compounds against decomposition, the method including applying to the teeth a composition comprising:
   (i) from about 0.1 to about 10% by weight of a peroxygen compound selected from the group consisting of urea peroxide, calcium peroxide, hydrogen peroxide, salts of perborate, salts of persilicate, salts of perphosphate and salts of percarbonate;
   (ii) from about 0.01 to about 5% by weight of a physiologically-acceptable fluoride-containing compound to inhibit formation of caries on teeth selected from the group consisting of sodium fluoride, potassium fluoride, calcium fluoride, magnesium fluoride, stannous fluoride, stannous monofluorophosphate, sodium monofluorophosphate and copper fluoride; and
   (iii) from about 0.01 to about 10% by weight of a zinc compound to stabilize the peroxygen compound against decomposition by the fluoride-containing compound, the zinc compound being selected from the group consisting of zinc borate, zinc bromide, zinc carbonate, zinc hexafluorosilicate, zinc pyrophosphate, zinc silicate, zinc sulphate, zinc titanate, zinc acetate, zinc benzoate, zinc citrate, zinc glycinate, zinc lactate, zinc phenolsulphonate, zinc salicylate, zinc tartrate, zinc acetylacetonate, zinc maleate, zinc succinate, zinc ascorbate, and zinc gluconate.

7. A composition according to claim 1 wherein the peroxygen compound is present in an amount from 1.5 to 5% by weight.

8. A composition according to claim 1 further comprising from about 20 to about 95% by weight of water.

9. A composition according to claim 8 further comprising polyoxyethylenepolyoxypropylene copolymer in an amount from 18 to 25% by weight.

10. A composition according to claim 9 further comprising glycerol in an amount from about 5 to about 50% by weight.

11. A composition according to claim 10 further comprising adjunct minor ingredients selected from the group consisting of colorant, flavor and antioxidant, each present in an effective amount for their respective stated purpose.

12. A method according to claim 6 wherein the peroxygen compound is present in an amount from 1.5 to 5% by weight.

13. A method according to claim 6 further comprising from about 20 to about 95% by weight of water.

14. A method according to claim 13 further comprising polyoxyethylenepolyoxypropylene copolymer in an amount from 18 to 25% by weight.

15. A method according to claim 14 further comprising glycerol in an amount from about 5 to about 50% by weight.

16. A method according to claim 15 further comprising adjunct minor ingredients selected from the group consisting of colorant, flavor and antioxidant, each present in an effective amount for their respective stated purpose.

17. A method according to claim 6 wherein the zinc compound is zinc citrate.

* * * * *

UNITED STATES PATENT AND TRADEMARK OFFICE
CERTIFICATE OF CORRECTION

PATENT NO. : 5,372,802
DATED : December 13, 1994
INVENTOR(S) : Barrow et al.

It is certified that error appears in the above-indentified patent and that said Letters Patent is hereby corrected as shown below:

On the title page, items [75] and [19] the first inventors last name should be changed from "Barrows" to --Barrow--.

Signed and Sealed this

Twenty-eight Day of March, 1995

Attest:

BRUCE LEHMAN

Attesting Officer     Commissioner of Patents and Trademarks